US006748164B1

United States Patent
Kuzyk

(10) Patent No.: US 6,748,164 B1
(45) Date of Patent: Jun. 8, 2004

(54) PLASMA THAWING SYSTEM

(75) Inventor: Roman Kuzyk, Trenton, NJ (US)

(73) Assignee: Photo-therm, L.P., Trenton, NJ (US)

( * ) Notice: Subject to any disclaimer, the term of this patent is extended or adjusted under 35 U.S.C. 154(b) by 395 days.

(21) Appl. No.: 09/703,257

(22) Filed: Oct. 31, 2000

(51) Int. Cl.[7] ................................................. A61F 7/08
(52) U.S. Cl. ....................... 392/443; 392/470; 604/6.13
(58) Field of Search .................... 422/44, 46; 604/6.13, 604/6.11, 6.14, 6.15, 903; 392/443, 470, 471; 165/104.31

(56) References Cited

U.S. PATENT DOCUMENTS

| | | | | | |
|---|---|---|---|---|---|
| 2,845,929 | A | * | 8/1958 | Strumia | 604/113 |
| 3,518,393 | A | * | 6/1970 | Besseling | 219/772 |
| 4,486,389 | A | * | 12/1984 | Darnell et al. | 422/307 |
| 5,147,330 | A | * | 9/1992 | Kogel | 604/245 |
| 5,243,833 | A | * | 9/1993 | Coelho et al. | 62/376 |
| 5,779,974 | A | | 7/1998 | Kuzyk | |
| 6,007,773 | A | | 12/1999 | Kuzyk | |

FOREIGN PATENT DOCUMENTS

| | | |
|---|---|---|
| DE | 3741051 | 6/1989 |
| EP | 0318924 B1 | 11/1988 |

OTHER PUBLICATIONS

Thermogenesis, Plasma Thawers, Advertisement.
Photo–Therm, Plasma Thawing System—Cyto–therm III T, Advertisement.
Photo–Therm, Plasma Thawing System—Cyto–therm CT–S, Advertisement.

* cited by examiner

Primary Examiner—Thor Campbell
(74) Attorney, Agent, or Firm—Donald R. Piper, Jr.; Dann, Dorfman, Herrell and Skillman

(57) ABSTRACT

A heating apparatus is provided for heating a medical product such as a bag of frozen plasma or blood. The apparatus includes a reservoir for holding a supply of heating liquid. At least one heating compartment is provided for holding a bag of frozen plasma or blood. At least one bladder is disposed within the heating compartment for engaging the medical product within the heating compartment and for receiving heating fluid from the reservoir to heat the medical product. A controller is provided for controlling the heating of the medical product. A heater operates under the control of the controller for providing heat to the heating fluid. A pump operates under the control of the controller for pumping the heating fluid from the reservoir to the bladder to effect heat transfer to the medical product in engagement with the bladder. A rocker operates under the control of the controller for agitating or rocking the medical product within the heating compartment to facilitate thawing of the medical product.

58 Claims, 4 Drawing Sheets

PLASMA THAWING SYSTEM

FIELD OF THE INVENTION

This invention relates to plasma thawing systems for thawing frozen bags of plasma or blood, and in particular, to dry plasma thawing systems in which frozen bags of plasma are thawed without direct submersion into a liquid bath.

BACKGROUND OF THE INVENTION

Storing frozen plasma and then thawing it for transfusions is common practice at health care facilities. Typically, bags of plasma are frozen to preserve the plasma for subsequent use. For this purpose, plasma is usually stored frozen in a sealed prepackaged pouch or bag. Prior to use, the frozen plasma is thawed and heated to a selected temperature.

Before a frozen bag of plasma can be used for a transfusion, the frozen plasma must first be heated to a desired transfusable temperature. To accomplish the thawing of the frozen plasma, a bag of frozen plasma may be placed directly into a liquid bath which is heated to a predetermined temperature to raise the temperature of the plasma. One of the problems with using this type of wet bath to effect plasma thawing is that contamination of the entire bath will occur if a plasma bag inadvertently leaks during the thawing process. Another problem is that contaminants in the bath may be transferred to the bag of plasma. Consequently, as an alternative to thawing the plasma by direct insertion into a wet bath, an overwrap bag can be used to protect the blood product bag and to isolate the bag in case of breakage. The disadvantage of overwrap bags is that they are wet on the outside and handling such bags is inconvenient and creates a breeding ground for bacteria.

A better approach is dry thawing without requiring exposure to water, but ensuring that the temperature of the blood product never exceeds body temperature. Dry thawing with the plasma bag disposed in a vertical orientation has disadvantages because the bath must be drained for loading and refilled for thawing. Horizontal dry thawing overcomes this disadvantage. A dry system of heating the plasma has been utilized in which plasma bags are placed in contact with a bladder filled with heating fluid. The dry system of thawing functions to isolate the plasma bags from the heating fluid while still effecting heat conduction to the bags.

While the use of a dry, or indirect, heating system reduces the possibility that the heating fluid will become contaminated during bag leakage, contamination problems still exist when multiple plasma bags are thawed in an apparatus at the same time. Even in a dry system, if one of the plasma bags leaks, then all of the plasma bags become tainted and must be discarded. Another problem with conventional dry horizontal systems in which one or more plasma bags rest horizontally upon bladders to effect heating is that air pockets or air bubbles have a tendency to form along the top surface of the bladder which is in contact with the bag of plasma. The trapped air pocket acts as an insulator between the heating fluid and the plasma bag thereby decreasing the effectiveness of the thawing apparatus both in terms of time and energy costs. Therefore, it would be advantageous if a dry frozen plasma thawing system was capable of more efficiently thawing more than one plasma bag while preventing contamination from a single bag from causing the whole lot of plasma bags to be discarded.

SUMMARY OF THE INVENTION

In accordance with the present invention, a heating apparatus is provided for heating a medical product to a selected temperature. More specifically, the heating apparatus functions to provide heat to a medical product, such as frozen bags of blood or plasma, in order to thaw the frozen blood or plasma to a predetermined temperature for use in a selected medical procedure.

The heating apparatus includes a reservoir for holding a supply of heating fluid, such as water. A heating bladder is provided for engaging and heating the medical product. The bladder functions to receive heating fluid from the reservoir to effect indirect heat transfer from the heating fluid to the medical product. The bladder may include a bottom portion upon which a bottom surface of the medical product may rest and a top portion for covering a top surface of the medical product. The top portion and the bottom portion of the bladder are in fluid communication so that the heating fluid can transfer between the top portion and the bottom portion of the bladder during heating of the medical product. Such fluid communication allows any trapped air to flow from the bottom portion to the top portion so as to be out of contact with the medical product. The bladder may be in the form of an elongated bladder which may be folded in half so that one half of the bladder serves as the top portion and the other half of the bladder serves as the bottom portion so as to fold over and envelope the medical product.

A controller may be provided for controlling the heating of the medical product. A heater operates under the control of the controller for heating the heating fluid to a selected temperature. The heater may include a heating element disposed within the reservoir to effect the desired heating of the heating fluid.

A pump may be provided for operation under the control of the controller for pumping the heating fluid from the reservoir to the bladder. The pump may operate in a continuous mode or in a cyclical mode so as to control the flow of heating fluid to the bladder. A drain is provided in association with the bladder so that heating fluid from the bladder may drain back to the reservoir for reheating. The drain may be a passive gravity flow drain or an active drain that operates under the control of the controller. In operation, heating fluid that is heated in the reservoir may be pumped by the pump to the bladder to effect heat transfer to the medical product in engagement with the bladder. From the bladder, the heating fluid may be drained back to the reservoir where the heating fluid may be reheated by the heater to provide circulation of heating fluid through the bladder.

An agitator may be provided to agitate the medical product within the heating chamber to facilitate thawing. For this purpose, the agitator may be in the form of a motor-controlled rocker that rocks the heating chamber in order to promote thawing of the medical product within the heating chamber. In specific application, the rocker may operate under the control of the controller.

In order to detect any leakage of liquid within a heating chamber, a leak sensor may be provided. For example, sensor terminals may be provided within the heating chamber for detecting the presence of liquid within the chamber. The controller is responsive to the leak sensor for outputting an indication of the presence of liquid in the heating compartment. The controller may function to activate a visual or audible alarm reflecting a leak condition. Alternatively, the controller may function to completely stop the heating of the medical product in response to the detection of liquid in the heating compartment by the leak sensor.

A temperature probe may also be provided in the heating compartment for detecting the temperature of the medical product within the heating chamber. For this purpose, the temperature probe may be disposed within the heating compartment to engage the medical product to detect the temperature of such medical product. The controller operates in response to the temperature probe to control the heater to regulate the temperature of the medical product. In a programmed mode of operation, the controller may function to control the operation of the pump in response to the temperature probe to further regulate the temperature of the medical product. The controller may also operate in response to the temperature probe to stop the heating of the medical product when the temperature of the medical product detected by the temperature probe reaches a selected temperature.

An air filter may be provided in communication with the reservoir for filtering air relative to the reservoir. For example, when heating fluid is pumped from the reservoir to the bladder, ambient air is drawn into the reservoir through the filter to effect filtering of the intake of ambient air. Likewise, when heating fluid is drained from the bladder back into the reservoir, air in the reservoir may be exhausted through the filter to effect filtering of the exhaust air.

The heating apparatus may also be provided with a plurality of separate heating compartments and a plurality of bladders with at least one bladder disposed in each heating compartment to effect the simultaneous heating of multiple bags of frozen plasma. The individual heating compartments are separate from one another so that any leakage of liquid in one compartment is contained from any other compartment. Accordingly, if a medical product leaks into one compartment thereby contaminating such compartment, such contamination is isolated from the medical products in the separate heating compartments.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
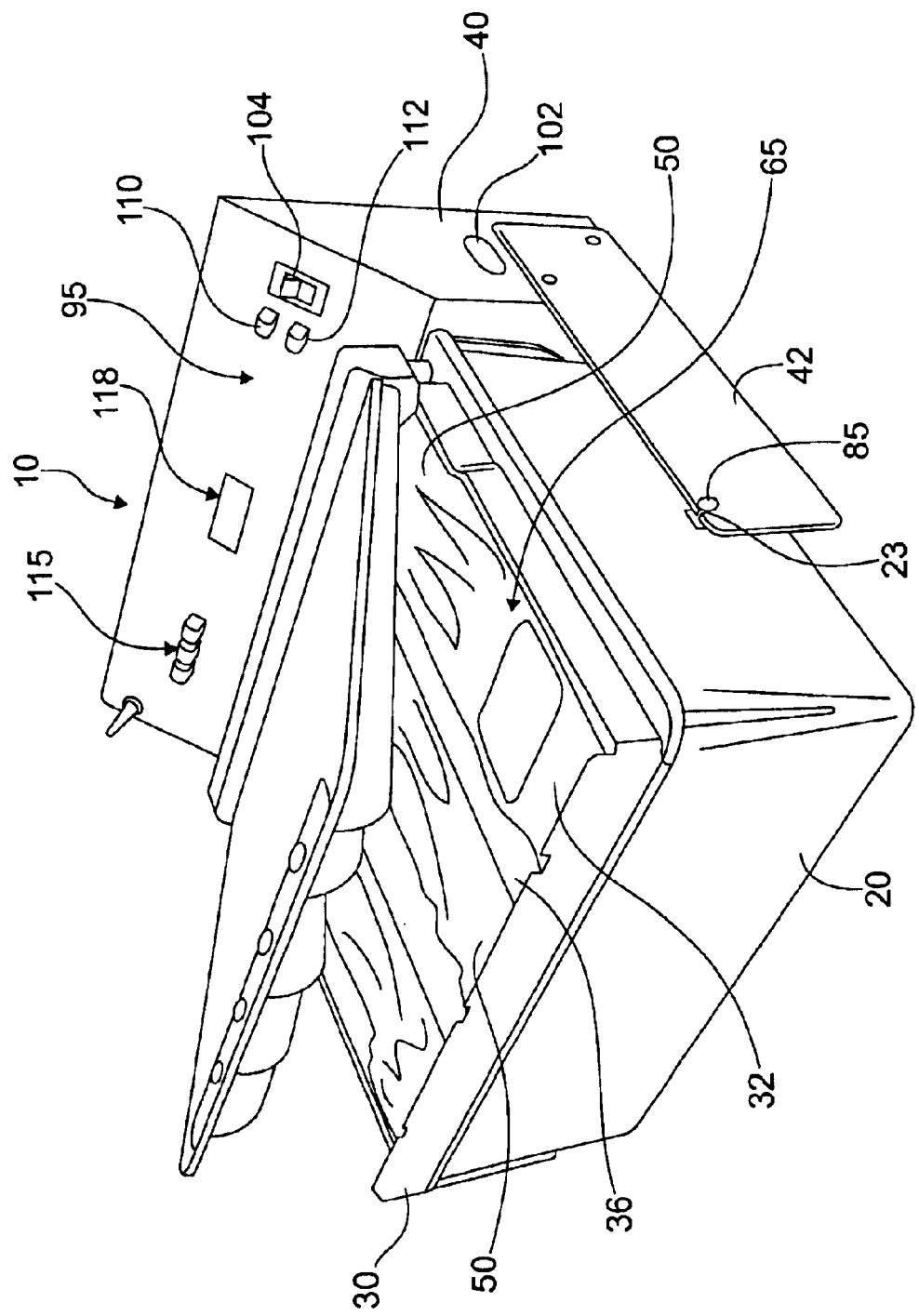
FIG. 1 is a perspective view of a heating apparatus, in the form of a dry plasma thawer, for heating a medical product in accordance with the present invention.

Referring now to the Figures in general, wherein like reference numerals refer to the same components across the several views, there is shown a dry plasma thawer 10 for heating bags of frozen blood or plasma to a desired temperature to effect thawing.

Figure 2:
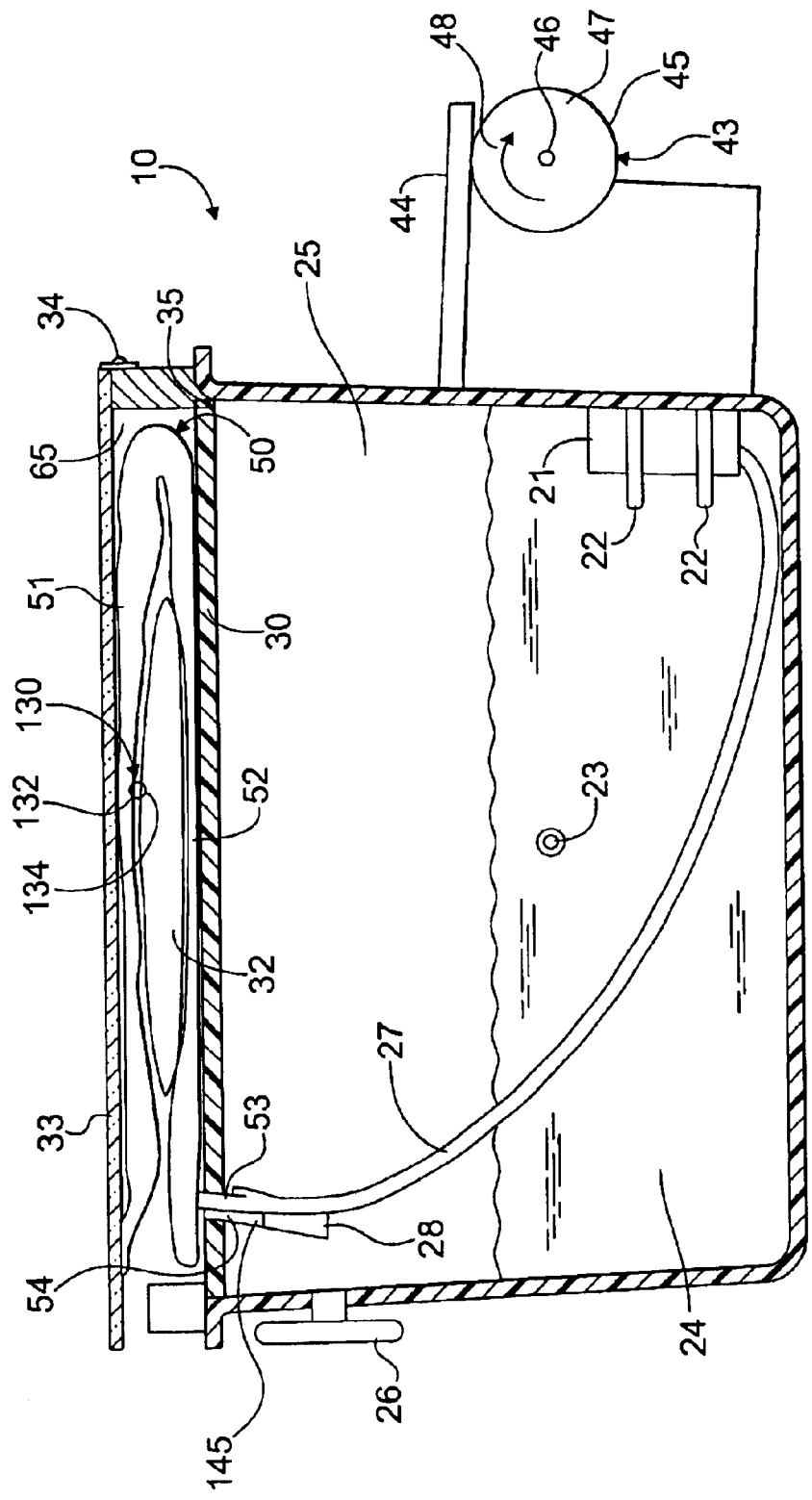
FIG. 2 is a schematic side elevation view, in partial cross section, of the dry plasma thawer.

Referring now to FIGS. 1 and 2, the dry plasma thawer 10 includes a housing 20, which provides a sealed internal reservoir basin 24 to hold a supply of heating liquid such as water for supply to a heating bladder 50 to effect heat transfer to a bag of frozen plasma. An air volume 25 is contained within the housing 20 above the water level in the reservoir basin 24. The housing 20 is constructed from a thermally insulative material to prevent heat loss from the heating liquid to atmosphere.

The dry plasma thawer 10 includes a rack 30 removably mounted on the housing 20 for providing a plurality of separate individual heating components 65 for receiving and holding individual medical products, such as frozen bags of plasma or blood, for purposes of heating and thawing the medical products. To effect the desired heating of the frozen bags of plasma, a separate heating bladder 50 is positioned and contained within each heating compartment 65. During use, a frozen bag of plasma is positioned within a respective heating compartment for envelopment by and thermal contact with the bladder 50. Heating liquid is then circulated from the basin 24 through the bladder 50 to effect heat transfer to the medical product. In order to control the heating and thawing process, the heating liquid is heated and circulated through each bladder 50 under the control of a controller 90 which can be programmed for operation by a user via control panel 95. The controller 90 is housed within control housing 40 and functions to control the flow and time period and temperature of heating of the heating liquid to regulate the heating and thawing of the medical product.

A heater 22 operating under the control of controller 90 is provided to heat the heating liquid in the reservoir basin 24 to a selected temperature. The heated liquid is then pumped by a pump 21 operating under the control of controller 90 to the heating bladders 50. After heat from the heating liquid is transferred to the frozen bags of plasma resting within the respective heating bladders, the heating liquid is drained from the bladders back to the reservoir basin 24 through drain outlet 54.

As shown in FIG. 2, the pump 21 and the heater 22 are situated within reservoir basin 24, preferably mounted to a sidewall of the housing 20. The pump 21 and the heater 22 are electrically connected to a source of power 100 through power inlet 102. The pump 21 and the heater 22 can be powered under the control of the controller 90 by a power switch 104 connected in series with the power source. The control panel 95 provides various inputs to effect user control of the apparatus. For example, a start button 110 and a stop button 112 are provided to allow the user to manually start or stop a heating run. In addition, program control inputs 115 are provided on the control panel 95 to enable a user to operate the heating apparatus under program control of the controller 90. The control inputs 115 may include a + button, a − button, and an ENTER button to enable the entry of program input of desired control parameters. For example, the inputs 115 may be used to enter any desired input information such as temperature settings, thaw times, pump times, heating times, and/or start and stop times. To enable the entry of run times, a timer 119 is provided for the controller 90. The timer 119 is responsive to selected program inputs entered by a user with control inputs 115 to control the time period of operation. Alternatively, an endpoint temperature setting may be entered at inputs 115 so that temperature feedback is utilized to stop the heating apparatus when the plasma bag reaches the selected temperature. Output information, such as entered settings or operation information, may be displayed to the user on output display 118.

In operation, when the heater 22 is activated, the heater warms the water in the basin 24 to a desired temperature for thawing the frozen plasma bag 32. The heated water is subsequently pumped by the pump 21 into the heating bladder 50 housed within a heating compartment of the rack via an inlet conduit 27. The inlet conduit 27 is preferably formed of a polyethylene tubing, polyvinyl chloride tubing, flexible copper tubing, or some other comparable flexible material. The inlet conduit 17 is sealably connected to an inlet 53 on the bladder 50. After circulation through the bladder, the water from the bladder 50 is drained back into the reservoir basin 24 via an outlet conduit 28 sealably connected with an outlet 54 on the bladder.

In order to prevent contaminants from entering the reservoir basin 24, a filter 26 is provided on housing 20 to filter air relative to the reservoir basin 24. During the pumping stage, for example, water pumped to the bladder from the reservoir basin must be displaced by an equal volume of air 25, which enters the basin 24 through air filter 26. Likewise, as the bladder 50 drains, and water re-enters the basin 24 and causes air to be exhausted through the air filter 26. As the air 25 passes through air filter 26, contaminants in the air, which would have otherwise entered into the reservoir basin 24, are filtered out.

In order to provide temperature feedback during operation, a temperature probe 130 is disposed within at least one heating compartment 65 of the rack 30 for engaging a frozen bag of plasma contained within the heating compartment. The temperature probe 130 functions to detect the temperature of the frozen plasma bag. The temperature probe is connected with the controller 90 in order to permit the controller 90 to control the heating process in response to the temperature detected by the heating probe 130. For example, the controller 90 may be programmed to regulate the heater 22 or the pump 21 in response to temperature feedback from the temperature probe to control or regulate the heating process. Alternatively, the controller 90 may be programmed to stop the heating process entirely when the temperature of the plasma bag detected by the temperature probe reaches a selected or predetermined amount. In order to obtain proper temperature readings, a portion 132 of the probe, such as the top portion of the probe shown in FIG. 2, which is in contact with the bladder is insulated to prevent detection of the temperature of the bladder. However, the portion 134 of the probe 130 in contact with the plasma bag remains uninsulated so that an accurate temperature reading from the plasma bag may be obtained.

In order to facilitate the thawing of the plasma bags held within the heating compartments 65 of the rack 30, a motor-powered agitator 43 is provided to move and agitate the plasma bags. For this purpose, the agitator 43 is provided in the form of a motor-driven rocker which functions to rock the rack 30 up and down during the thawing process. The rocker 30 may operate under program control of the controller 90 to better regulate the heating process. The rocker 43 includes a lever 44, having one end tangentially on a motor-driven rotating cam 45. The other end of the lever cooperates with the rack to effect the desired rocking of the rack. The cam 45 is connected to a motor. In a desired application, the rocker motor may be controlled by controller 90 so that the motor can be switchably activated under program control. The cam 45 includes a rotational center 46 that is offset from the geometric center of the cam 45. In this configuration, when the cam 45 is rotated about its rotational center 46, the lever arm 44 will be cyclically raised and lowered as the wide portion 47 and the narrow portion 48 of the cam 45 are cycled with the end of the lever 44. The other end of the lever is connected with the basin 24 so that the rack 30 which is supported on the basin and holds the frozen plasma bags is gently rocked about pivot axis 85. As shown in FIG. 1, the pivot axis is disposed in a slot on an external support arm 42. The rocking of the rack 30 causes a gentle rocking agitation of the frozen plasma bags 32, thereby accelerating the thawing process.

Referring now to FIG. 2, the heating rack 30 is disposed above the reservoir basin 24 and is situated on top of a seal 35. The seal 35 is disposed between the rack 30 and the reservoir housing 20 in order to provide an airtight seal to prevent contaminants from entering the reservoir basin 24 without being filtered by air filter 26. Furthermore, the rack 30 includes a clear plastic lid 33 which functions to close the rack to prevent heat from escaping during the heating process. The clear plastic lid also permits visual inspection of the plasma bags without lifting the lid 33. The lid 33 is connected to rack 30 at one end by a floating hinge 34, which allows the lid 33 to be lifted and retained in open position without requiring the lid to be removed from rack 30. The lid 33 may be designed to hold a top portion 51 of each bladder 50 within the lid while a bottom portion 52 of each bladder is held within a respective heating compartment of the rack. In this arrangement, the lid functions to lift the top portion 51 of each bladder 50 out of contact with a bottom portion 52 of each bladder about a center fold line of the bladder thereby exposing the bottom portion of each bladder as a resting bed for the horizontal placement of a frozen plasma bag. When the lid is closed, the top potion 51 of each bladder will be moved into covering engagement with the plasma bag resting upon the bottom portion 52 of the bladder 50 thereby enveloping the plasma bag within the bladder.

Figure 3:
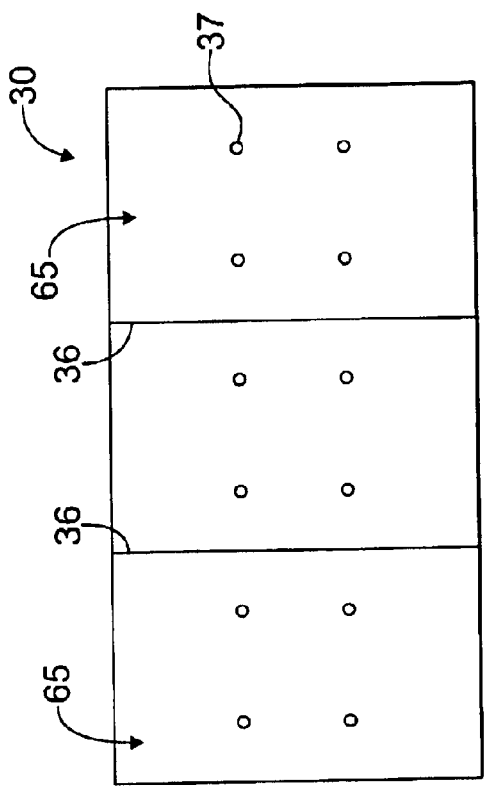
FIG. 3 is a schematic plan view of a rack of multiple heating compartments for housing individual heating bladders wherein a leak sensor is disposed on the bottom of each of the compartments.

In order to hold multiple plasma bags separate from one another, the rack 30 contains dividing partitions 36 which functions to sealably partition the rack into separate, isolated heating compartments. A separate frozen plasma bag 32 may be disposed within each compartment to isolate each plasma bag from one another. The partitions 36 provide separate sealed compartments 65 on the rack that prevent any leakage in one compartment from spreading to a neighboring compartment. In order to enable the detection of any liquid within a compartment, leak sensors 37 are disposed at the bottom of each compartment 65 as shown in FIG. 3. The sensors 37 function to monitor if any leaks occur in an individual compartment 65. The leak sensors 37 may be in the form of paired sensors that function to detect the presence of liquid across the paired sensors. The leak sensors 37 may be connected with the controller 90 so that operation of the heating apparatus can be controlled in response to the detection of liquid in one of the heating compartments 65. For example, the controller may function to signal an alarm 150, such as an audible alarm or a visual alarm. A visual alarm may be provided as an indication on output display 118. Alternatively, the controller 90 may function to stop the heating process entirely in response to the detection of liquid in a heating compartment by leak sensors 37.

Figure 4:
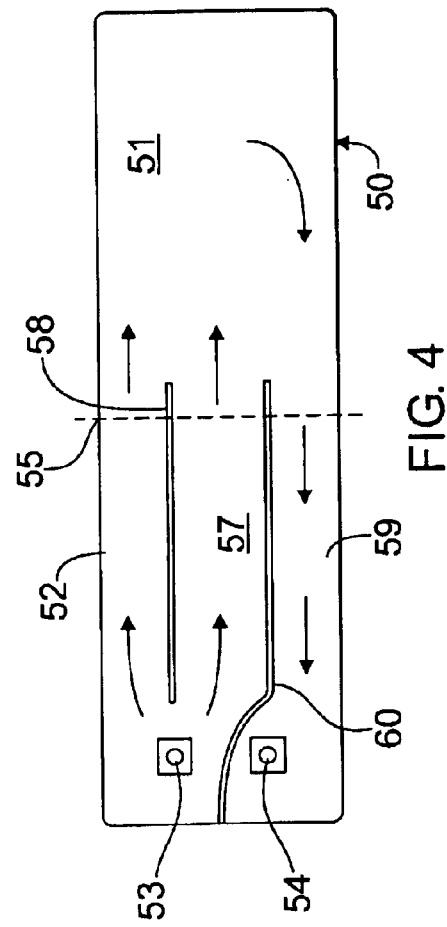
FIG. 4 is a schematic plan view of an elongated heating bladder contained within each of the heating chambers.
Figure 5:
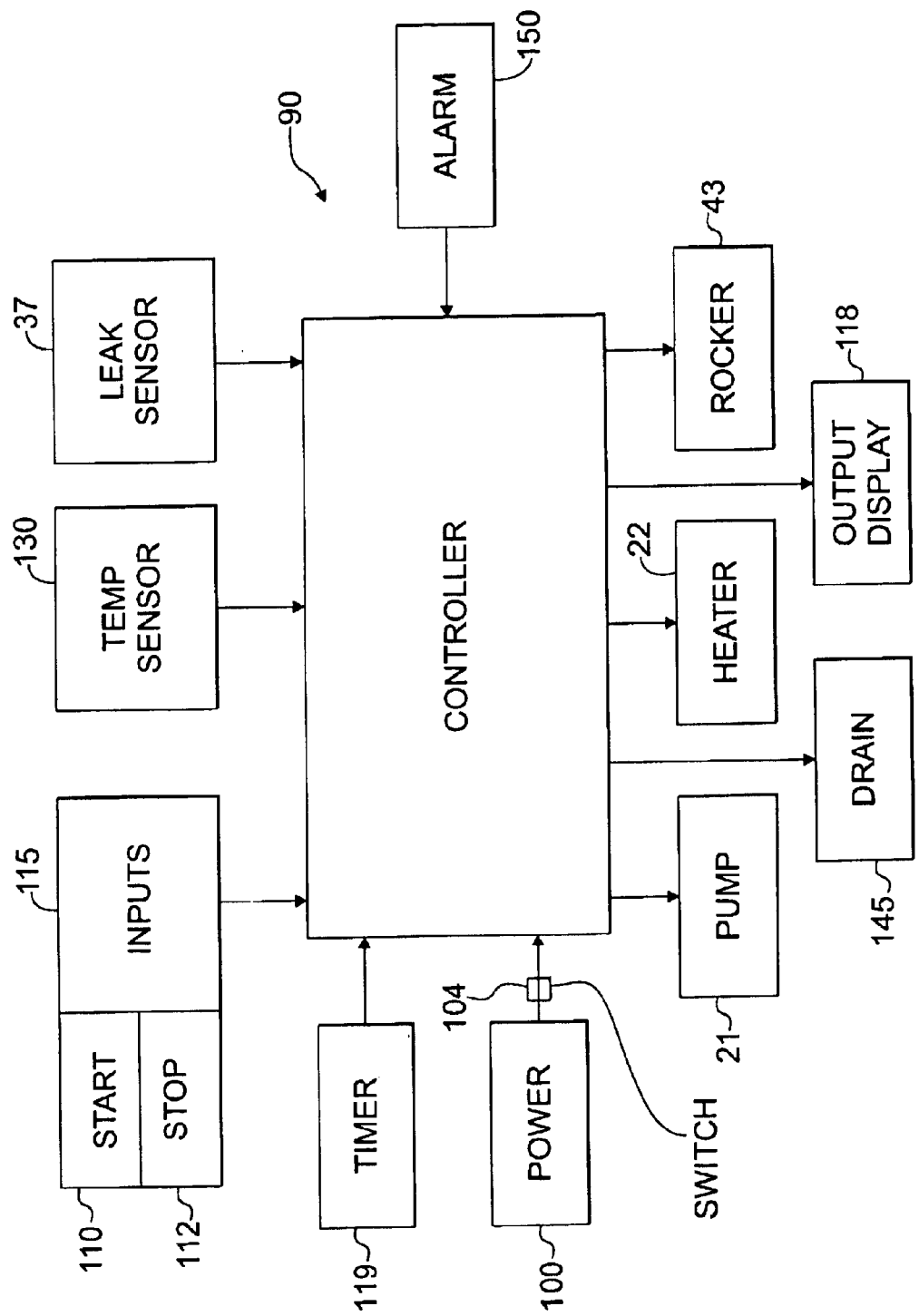
FIG. 5 is a block diagram of the control circuitry for the heating apparatus.

Referring now to FIGS. 2 and 4, the bladder 50 is depicted in an unfolded, laid-open configuration. The bladder 50 is made from a heat conductive material to facilitate heat transfer between the heating liquid and the frozen plasma bag. The bladder is sufficiently elongated so that the bottom portion 52 of the bladder spans the length of the heating compartment while the top portion 51 spans the length of the covering lid. The bladder folds along a fold line 55 positioned adjacent hinge 34 so that the top and bottom portions of the bladder may be unfolded open and folded closed as the lid 33 is opened and closed. The bladder 50 is disposed within a respective heating compartment 65 of the rack 30 so that the inlet 53 and the outlet 54 on the bottom portion of the bladder are directed downward toward the reservoir basin 24. As shown in FIG. 4, the bladder includes a pair of inlet channels 57 internal to the bladder separated by a channel wall 58 which extends from the inlet 53 on the bottom portion 52 of the bladder beyond the fold line 55 and into the top portion 51 of the bladder. The extension of the channel wall 58 into the top portion 51 of the bladder functions to ensure a flow of heating liquid from the inlet 53 on the bottom portion 52 of the bladder into the top portion 51 of the bladder. An outlet channel 59 is provided internally of the bladder 50 to direct a flow of heating liquid from the top portion 51 of the bladder to the outlet 54 on the bottom portion of the bladder for drainage back to the reservoir basin 24. A channel wall 60 separates the inlet channels 57 from the outlet channel 59. The channel wall 60 extends the entire length of the bottom portion 52 of the bladder and into the top portion 51 of the bladder. As shown in FIG. 4, the channel wall 60 is disposed so that the transverse width of the inlet channels 57 is wider than transverse width of the outlet channel 59 so that the rate of flow of heating liquid into the bladder will not be slower than the rate of drainage of heating liquid from the bladder. As a result, the bladder will fill with heating liquid while a continuous circulation of heating liquid through the bladder is maintained. As heating liquid is pumped from the basin 24 into the bladder, heating liquid in the bladder will be forced through outlet 54. In an alternative arrangement, a drain regulator 145 may be provided at outlet 54 to positively control the drain rate from the bladder. The drain regulator, such as a drain valve, may be controlled by the controller 90 to more actively control the opening and closing of the drain to better regulate the drainage of heating liquid from the bladder. When a drain regulator is employed, heating liquid may be pumped and retained in the bladder for a selected time period before the drain regulator 145 is actuated by the controller 90 to drain the heating liquid from the bladder.

In operation, a frozen plasma bag 32 is horizontally laid between the top portion 51 and bottom portion 52 of the bladder 50. The elongated bladder 50 is folded over itself at fold line 55 by the closing of the lid 33 thereby causing the bladder to envelope the frozen plasma bag 32. The bladder thereby makes thermal contact with the entire outer surface of the frozen plasma bag 32. In this folded configuration, the top portion of the bladder remains in fluid communication with the bottom portion of the bladder so that heating liquid can circulate between the top and bottom portions. Since the bladder 50 is folded around the frozen plasma bag 32 any air bubbles, which effectively act as a thermal insulator, that might have been trapped in the bottom portion of the bladder will pass or flow to the top portion of the bladder. Any such air bubbles will then rise to the highest area of the top portion 51 of bladder 50 and out of thermal contact with the frozen plasma bag 32. As a result, the overall surface area of the frozen plasma bag 32 held in direct thermal contact with the heating liquid in the bladder 50 is increased.

In view of the foregoing disclosure, a partitioned rack has been described which isolates several plasma bags from one another during a thawing procedure so that a rupture in any one of the plasma bags will be contained within its own respective chamber to avoid cross contamination of the remaining plasma bags. As a result, valuable plasma, which would have otherwise been discarded in the event of a leak, is preserved. Furthermore, an elongated bladder has been described which completely envelopes and maintains thermal contact with a frozen plasma bag whereby any air bubbles trapped within the bladder are relocated to an area of the bladder that is not in direct thermal contact with the plasma bag, thereby increasing the efficiency of the thawing unit and reducing the amount of critical time that a plasma bag takes to thaw.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A heating apparatus for heating a medical product comprising:

(a) a reservoir for holding a supply of heating fluid;

(b) at least one heating compartment;

(c) at least one bladder disposed within the heating compartment in fluid communication with the reservoir for engaging the medical product within the heating compartment and for receiving heating fluid from the reservoir to heat the medical product, the bladder including a bottom portion upon which a bottom surface of the medical product rests and a top portion for covering a top surface of the medical product wherein the top portion and the bottom portion are in fluid communication so that fluid transfers between the top portion and the bottom portion during heating of the medical product;

(d) a controller for controlling the heating of the medical product;

(e) a heater under the control of the controller for heating the heating fluid;

(f) a pump under the control of the controller for pumping the heating fluid from the reservoir to the bladder; and (g) a rocker under the control of the controller for rocking the medical product within the heating compartment.

2. The heating apparatus of claim 1 comprising a leak sensor within the heating compartment for detecting liquid within the heating compartment.

3. The heating apparatus of claim 2 wherein the controller is responsive to the leak sensor for outputting an indication of the presence of liquid in the heating compartment.

4. The heating apparatus of claim 2 wherein the controller is responsive to the leak sensor for stopping the heating of the medical product in response to the detection of the presence of liquid in the heating compartment.

5. The heating apparatus of claim 1 comprising a temperature probe in the heating compartment for engaging the medical product to detect the temperature of the medical product.

6. The heating apparatus of claim 5 wherein the controller is responsive to the temperature probe to control the heater to regulate the temperature of the medical product.

7. The heating apparatus of claim 5 wherein the controller is responsive to the temperature probe to control the pump to regulate the temperature of the medical product.

8. The heating apparatus of claim 5 wherein the controller is responsive to the temperature probe for stopping the heating of the medical product when the temperature of the medical product detected by the temperature probe reaches a selected temperature.

9. The heating apparatus of claim 1 comprising an air filter in communication with the reservoir for filtering air relative to the reservoir.

10. The heating apparatus of claim 1 comprising a plurality of the heating compartments and a plurality of the bladders wherein at least one bladder is disposed in each heating compartment, the heating compartments being separate from one another so that any leakage of liquid in one compartment is contained from any other compartment.

11. The heating apparatus of claim 1 comprising a frame and wherein at least the heating compartment is pivotally mounted about a pivot axis relative to the frame and wherein said rocker cooperates with the heating compartment to rock the heating compartment relative to the pivot axis.

12. The heating apparatus of claim 11 wherein the rocker comprises a cam and a lever arm engaging with the cam and cooperating with the heating compartment for rocking the heating compartment about the pivot axis.

13. A heating apparatus for heating a medical product comprising:
  (a) a heating chamber for holding and heating the medical product;
  (b) a controller for controlling the heating of the medical product; and
  (c) a liquid sensor in the heating chamber operably connected with the controller to detect liquid in the chamber.

14. The heating apparatus of claim 13 comprising an indicator responsive to the detection of liquid by the liquid sensor to indicate the presence of liquid in the chamber.

15. The heating apparatus of claim 14 wherein the indicator comprises an alarm indicator.

16. The heating apparatus of claim 15 wherein the alarm indicator comprises at least one of an audible alarm and a visual alarm.

17. The heating apparatus of claim 13 wherein the controller stops the heating of the medical product in response to the detection of liquid in the heating chamber.

18. A heating apparatus for heating a medical product, said heating apparatus comprising:
  (a) a heating medium having a heating fluid for heating the medical product;
  (b) a heater for supplying heat to the heating fluid;
  (c) a temperature probe for engagement with the medical product to detect the temperature of the medical product; and
  (d) a controller responsive to the temperature probe for adjusting the temperature of the medical product up to the temperature of the heating fluid of the heating medium to control the temperature of the medical product.

19. The heating apparatus of claim 18 wherein the controller is responsive to the temperature probe to maintain operation of the heater until the temperature of the medical product reaches the temperature of the heating fluid of the heating medium.

20. A heating apparatus for heating a medical product comprising:
  (a) a heating medium having a heating fluid for heating the medical product;
  (b) a heater for supplying heat to the heating fluid;
  (c) a temperature probe for engagement with the medical product and the heating medium having an insulated portion to insulate the temperature probe from the heating medium and an uninsulated portion for contacting the medical product to detect the temperature of the medical product; and
  (d) a controller responsive to the temperature probe for adjusting the temperature of the medical product up to the temperature of the heating fluid of the heating medium to control the temperature of the medical product.

21. A heating apparatus for heating a medical product comprising:
  (a) a reservoir for holding a supply of heating liquid;
  (b) a heating chamber for the medical product in fluid communication with the reservoir for receiving heating liquid from the reservoir to heat the medical product;
  (c) a pump for pumping heating liquid from the reservoir to the heating chamber; and
  (d) an air filter in communication with the reservoir to filter air relative to the reservoir.

22. The heating apparatus of claim 21 wherein the air filter filters ambient air that enters the reservoir as heating liquid is pumped from the reservoir to the heating chamber.

23. The heating apparatus of claim 21 comprising a drain associated with the heating chamber for enabling heating liquid from the heating chamber to be drained back to the reservoir wherein the air filter filters any air exhausted from the reservoir.

24. A heating apparatus for heating a plurality of medical products comprising:
  (a) a reservoir for holding a supply of heating fluid;
  (b) a plurality of heating chambers for holding and heating medical products, the heating chambers communicating with the heating fluid from the reservoir to heat the medical products, wherein the heating chambers are separate from one another so that any leakage of liquid in one chamber is contained from any other chamber; and
  (c) a controller for controlling the heating of the medical product.

25. A heating apparatus for heating a medical product comprising:
  (a) a reservoir for holding a supply of heating fluid;
  (b) a bladder in fluid communication with the reservoir to heat the medical product, the bladder including a bottom portion upon which a bottom surface of the medical product rests and a top portion for covering a top surface of the medical product wherein the top portion and the bottom portion are in fluid communication so that fluid transfers between the top portion and the bottom portion during heating of the medical product; and
  (c) a controller for controlling the heating of the medical product.

26. The apparatus of claim 25 wherein the controller controls a flow of heating fluid between the reservoir and the bladder.

27. The apparatus of claim 25 wherein the controller controls the temperature of the heating fluid.

28. The apparatus of claim 25 wherein the controller controls the time period that the medical product remains in engagement with the bladder containing heating fluid.

29. The apparatus of claim 25 comprising a rocker under the control of the controller for rocking the medical product.

30. The apparatus of claim 29 comprising a heating compartment for holding the bladder and a support frame and wherein at least the heating compartment is pivotally mounted about a pivot axis relative to the frame and wherein said rocker cooperates with the heating compartment to rock the heating compartment relative to the pivot axis.

31. The heating apparatus of claim 30 wherein the rocker comprises a cam and a lever arm engaging with the cam and cooperating with the heating compartment for rocking the heating compartment about the pivot axis.

32. The apparatus of claim 25 comprising a pump for providing a flow of heating fluid from the reservoir to the bladder under the control of the controller.

33. The apparatus of claim 32 comprising a drain cooperating with the bladder to drain heating fluid from the bladder back to the reservoir.

34. The apparatus of claim 33 comprising a drain regulator for the drain under the control of the controller for regulating the drainage of heating fluid back to the reservoir.

35. The apparatus of claim 25 comprising a heater for heating the heating fluid within the reservoir.

36. The apparatus of claim 35 wherein the heater operates under the control of the controller for heating the heating fluid within the reservoir to a selected temperature.

37. The apparatus of claim 36 comprising a temperature sensor for sensing the temperature of the medical product in contact with the bladder.

38. The apparatus of claim 37 wherein the controller operates in response to the temperature sensor to stop the heating of the medical product when the temperature sensor senses that the temperature of the medical product has reached a selected heating temperature.

39. The apparatus of claim 25 comprising an air filter in communication with the reservoir to filter air flow relative to the reservoir.

40. The apparatus of claim 39 comprising a housing for the reservoir and wherein the air filter filters air flow through the housing.

41. The apparatus of claim 25 comprising a heating compartment for holding the bladder and the medical product in communication with the bladder.

42. The apparatus of claim 41 comprising a leak detector positioned relative to the heating compartment to detect the presence of liquid within the heating compartment.

43. The apparatus of claim 42 wherein the controller operates in response to the leak detector to indicate the presence of liquid within the heating compartment.

44. The apparatus of claim 43 comprising an alarm actuated by the controller for indicating the presence of liquid in the heating compartment.

45. The apparatus of claim 42 wherein the controller is responsive to the leak detector for stopping the heating of the medical product in response to the detection of the presence of liquid in the heating compartment by the leak detector.

46. The apparatus of claim 25 comprising a plurality of the bladders and a plurality of heating compartments for holding the respective bladders wherein the heating chambers are separate from one another so that any leakage of liquid in one chamber is contained from any other chamber.

47. The apparatus of claim 25 wherein the bladder is an elongated bladder for folding around the medical product so that one end of the bladder serves as the bottom portion and the other end of the bladder serves as the top portion.

48. The apparatus of claim 47 comprising a heating compartment for holding the bottom portion of the bladder and a lid for closing the heating compartment wherein the top portion of the bladder is held on the lid.

49. The apparatus of claim 48 comprising a hinge for mounting the lid relative to the heating compartment so that the lid can be opened and closed relative to the heating compartment about the hinge.

50. The apparatus of claim 47 wherein the bladder includes an inlet for receiving a flow of heating fluid and an outlet for discharging a flow of heating fluid.

51. The apparatus of claim 50 wherein the bladder includes a channel wall for directing a flow of the heating fluid from the inlet to the outlet.

52. The apparatus of claim 50 comprising a channel wall extending from the bottom portion of the bladder into the top portion of the bladder and wherein the inlet and the outlet are disposed on the bottom portion of the bladder on opposite sides of the channel wall.

53. The apparatus of claim 52 wherein the inlet channel includes a larger volume than the outlet channel.

54. A heating apparatus for heating a medical product comprising:
 (a) a heating compartment for holding and heating the medical product;
 (b) a controller for controlling the heating of the medical product; and
 (c) a rocker for rocking the heating compartment to rock the medical product during heating.

55. The heating apparatus of claim 54 comprising a frame and wherein the heating compartment is pivotally mounted about a pivot axis relative to the frame and wherein said rocker cooperates with the heating compartment to rock the heating compartment relative to the pivot axis.

56. The heating apparatus of claim 55 wherein the rocker comprises a motor-driven cam and a lever arm engaging with the cam and cooperating with the heating compartment for rocking the heating compartment about the pivot axis.

57. The heating apparatus of claim 24 comprising a liquid sensor in each of the heating chambers, said liquid sensors each being operably connected with the controller.

58. The heating apparatus of claim 1 wherein said bottom and top sections of the bladder are in fluid communication and are continuous to facilitate passage from the bottom section to the top section of any gas bubbles that form within the bottom section.

* * * * *